United States Patent [19]

Mesek

[11] 4,005,713
[45] Feb. 1, 1977

[54] DISPOSABLE DIAPER HAVING TAB FASTENERS PROVIDED WITH A PULL STRING AND ATTACHED TO RELEASE SURFACES ON DIAPER FACING

[75] Inventor: Frederick K. Mesek, Downers Grove, Ill.

[73] Assignee: Johnson & Johnson, New Brunswick, N.J.

[22] Filed: Jan. 8, 1975

[21] Appl. No.: 539,487

[52] U.S. Cl. .............................. 128/287; 128/284
[51] Int. Cl.² .......................................... A61F 13/16
[58] Field of Search .......... 128/287, 286, 284, 289, 128/290, 293, 296; 24/DIG. 11

[56] References Cited

UNITED STATES PATENTS

| 2,714,889 | 8/1955 | Chambers | 128/284 X |
|---|---|---|---|
| 3,848,596 | 11/1974 | Pennau | 128/284 |
| 3,893,460 | 7/1975 | Karami | 128/287 |
| 3,901,239 | 8/1975 | Tritsch | 128/287 |
| 3,937,221 | 2/1976 | Tritsch | 128/287 |

Primary Examiner—John D. Yasko

[57] ABSTRACT

A disposable diaper having a moisture-impermeable backing sheet and a moisture-retaining layer on the backing sheet and forming a facing for direction toward an infant when the diaper is applied to that infant is provided with adhesive tab fasteners which are secured to the diaper backing sheet and which have a free working end removably attached to release regions on the diaper facing. The free working end of the tab fastener is provided with a pull string for separating the free working end from the surface of the release region.

6 Claims, 5 Drawing Figures

U.S. Patent  Feb. 1, 1977  Sheet 1 of 2  4,005,713
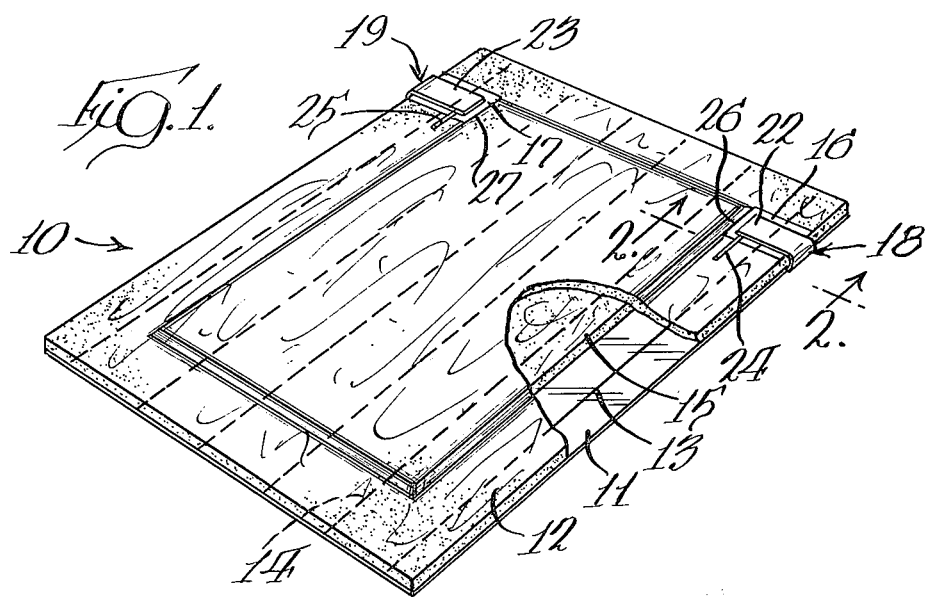
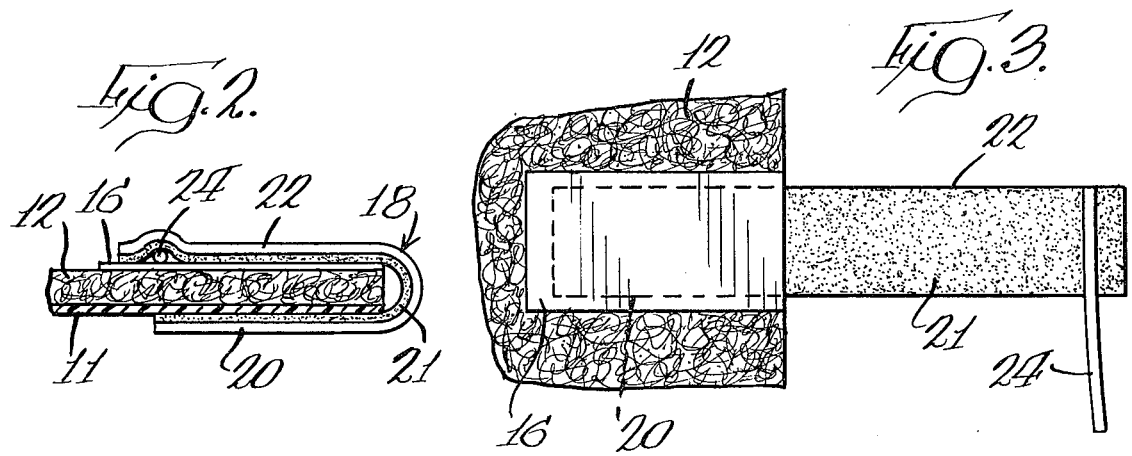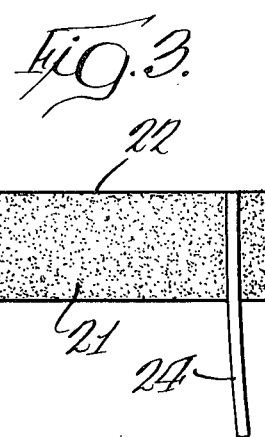
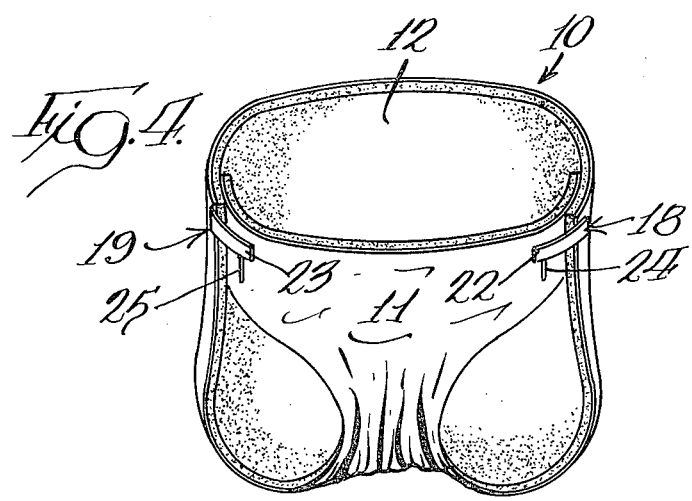

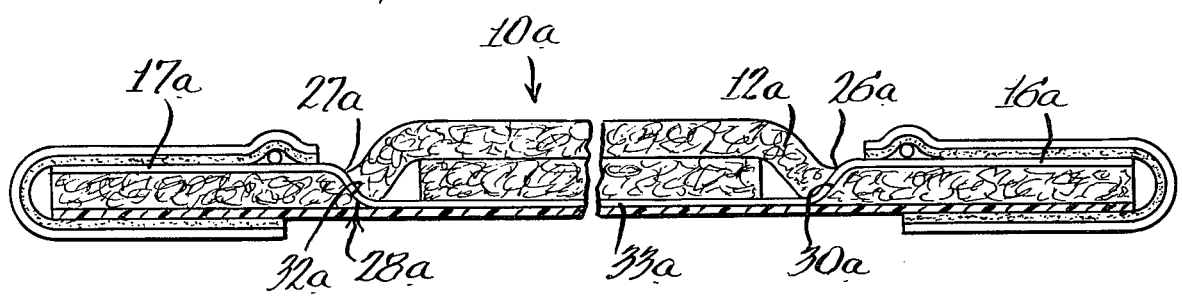

DISPOSABLE DIAPER HAVING TAB FASTENERS PROVIDED WITH A PULL STRING AND ATTACHED TO RELEASE SURFACES ON DIAPER FACING

BACKGROUND OF THE INVENTION

This invention relates to disposable diapers. More particularly, this invention relates to disposable diapers having adhesive tab-type fasteners.

Disposable diapers provide substantial advantages in convenience over conventional diapers and commonly have a generally quadrilateral configuration with straight or curvilinear longitudinal edges. Disposable diapers are conveniently secured about an infant by means of adhesive tape tabs which are affixed to the diaper along a longitudinal edge thereof, thus eliminating the need for extraneous fasteners, such as pins. In order to protect the adhesive surfaces of the tape tabs, usually a release sheet is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,776,234 to Hoey proposes to fold the tab over on itself at the diaper's edge and to adhesively attach a portion of the folded-over tab segment to the inside surface of the diaper in order to keep the tab from interfering with the manufacturing machinery and with the folding and packaging operations. This requires that the edge of the diaper backing sheet be folded over to present an attachment surface at the front or inside face of the diaper and a relatively involved tab design is necessary for this purpose. Also, undesirable tearing of the diaper facing fabric may result if such a tab is adhesively attached to the facing fabric of the diaper.

While the present disposable diaper closure systems utilizing adhesive tab-type fasteners having the adhesive surfaces thereof protected with readily removable release strips are relatively convenient to use, such closure systems have the disadvantage that the consumer has to dispose of the release strips when they are separated from the fasteners immediately prior to use. This is an inconvenience to the consumer who is placing a diaper on an infant at about the same time.

In an attempt to remedy the aforesaid disadvantage, U.S. Pat. No. 3,646,937 to Gellert shows a fastening tab which is provided with a release surface permanently attached to a diaper backing sheet at a margin thereof and folded inwardly over the diaper facing. In addition to requiring relatively involved manufacturing manipulations the teachings of Gellert also require special securement means to assure that the fastening tab will not separate from the release sheet prematurely during manufacture and handling of the diaper. According to Gellert, a portion of the tab fastener having a tacky surface also serves as a pull tab for assisting the separation of the tab fastener from the release sheet. Such an arrangement is undesirable, however, inasmuch as the tacky surface on the "pull tab portion" would be rendered relatively less tacky due to finger contact therewith during preparation of the diaper for ultimate use, thus the effective tacky surface available for securely fastening the diaper would be considerably and undesirably reduced.

The present invention, on the other hand, provides a release region on the diaper facing to which is removably attached a free working end of a tab fastener bearing a relatively aggressive adhesive. Finger contact with a tacky surface on the free working end is avoided and the separation thereof from the underlying release region on the diaper facing is facilitated by a pull string segment attached to the free working end.

SUMMARY OF THE INVENTION

The present invention contemplates a disposable diaper having a moisture-impermeable backing sheet which forms an outside surface for direction away from an infant, a moisture-retaining layer adhered to the backing sheet and having a facing which forms a diaper inside surface for direction toward the infant, a release region on the facing and situated near a longitudinal margin of the diaper, and tab fastener means having a fixed end secured to the diaper backing sheet and a free working end removably attached to the release region on the diaper facing. A pull string means is attached to the free working end for assisting in the separation of the free working end from the underlying release region.

BRIEF DESCRIPTION OF THE DRAWING

In the drawing,

FIG. 1 is a perspective view, partially broken away, showing a disposable diaper embodying the present invention;

FIG. 2 is a fragmentary sectional elevation on an enlarged scale, taken along plane 2-2 in FIG. 1;

FIG. 3 is an enlarged fragmentary plan view showing a disposable diaper having a tab fastener ready for use; and FIG. 4 is a perspective view showing the diaper of FIG. 1 in a configuration assumed when the diaper is placed about an infant.

FIG. 5 is a cross-sectional view showing another embodiment of the invention.

DESCRIPTION OF THE PREFERRED EMBODIMENTS

Referring to FIG. 1, disposable diaper 10 includes moisture-impermeable backing sheet 11 which forms a diaper outside surface for direction away from an infant, moisture-permeable facing sheet 12 substantially coextensive with backing sheet 11 and attached thereto by means of adhesive beads such as beads 13 and 14, and absorbent pad 15 which is sandwiched between facing sheet 12 and backing sheet 11 and anchored to backing sheet 11 by means of adhesive beads such as bead 14. Absorbent pad 15 and facing sheet 12 together comprise a moisture-retaining layer of diaper 10, and facing sheet 12 additionally provides a relatively soft facing which forms a diaper inside surface for direction toward the infant.

Release regions 16 and 17, usually in the form of a flexible strip of sheet material, e.g., a paper sheet or a polyolefin film, coated on one side with a silicone compound or similar release composition, and permanently attached by means of an adhesive or by heat bonding, to the surface of facing sheet 12 near opposed longitudinal margins of diaper 10. Alternatively, release regions 16 and 17 can also be produced by treating the appropriate surface portions of fibrous facing sheet 12 with a release composition. The desired release regions on facing sheet 12 near each opposed longitudinal margin of diaper 10 can also be provided as shown in FIG. 5 by lacing a release-coated strip or ribbon 28a of a sheet material transversely across diaper 10a and through slots 30a and 32a in facing sheet 12a so that a central portion 33a of the strip 28a or ribbon is under facing sheet 12a and the terminal portions 34a and 36a of the release-coated strip 28a or ribbon project through facing sheet 12a to form release regions 16a and 17a. In this particular embodiment slots in facing sheet 12a are provided at innermost boundaries 26a and 27a of respective release regions 16 and 17.

Adhesive tab fasteners 18 and 19 each comprise a fixed end permanently attached to diaper backing sheet 11 and a free working end, such as free working ends 22 and 23, removably held on respective release regions 16 and 17. As shown in FIG. 2, fixed end 20 of tab fastener 18 is attached to backing sheet 12 by means of pressure-sensitive adhesive layer 21 which is coextensive with tab fastener 18. Free working end 22 of tab fastener 18 is removably attached to the release surface of release region 16 by adhesive layer 21. Free working end 23 of tab fastener 19 is removably held on release region 17 in a similar manner. Preferably, the area of release regions 16 and 17 is greater than the area of free working ends 22 and 23 in contact therewith in order to allow for manufacturing tolerances.

Pull string segment 24 attached to free working end 22 extends therebeyond (FIGS. 2 and 3) and provides an effective means for peeling free working end 22 away from release region 16 when tab fastener 18 is about to be used for securing diaper 10 about an infant. Similar pull string segment 25 is attached to free working end 23 of tab fastener 19. A convenient manner of attachment for the pull string segments is by adhesive attachment to the respective adhesive layers on the free working ends of the tab fasteners. If desired, the pull string segment can also be embedded in the free working end, for example, in instances when the tab fasteners are made of thermoplastic tape stock, or the like. The pull string segment can be a piece of thread or cord, a monofilament segment, a braid, band, or ribbon, or similar means.

After the tab free working end has been separated from its corresponding release surface and assumes the position shown in FIG. 3 where free end 22 has been lifted from release region 16 exposing a tacky surface of pressure-sensitive adhesive layer 21, pull string segment 24 can be removed from tab free end 22, if desired. However, it is advantageous to leave pull string segment 24 in place because after diaper 10 has been applied to an infant as illustrated in FIG. 4 by affixing tab free end 22 to the outside surface of backing sheet 11, pull string segment 24 can also be used as an assist in subsequently removing the tab fasteners, such as tab 18, from their respective areas of affixation on diaper backing sheet 11 when the diaper becomes soiled and must be removed from the infant.

A suitable backing sheet material for the diaper embodying the present invention can be an opaque polyethylene web about 0.001 inch thick. Another suitable sheet material for this purpose is a polyethylene terephthalate web having a thickness of about 0.0005 inch.

Several different types of facing materials may be used for diaper facing sheet 12. For example, facing sheet 12 may be made up of a mixture of fibers consisting predominantly of inexpensive short cellulosic fibers, such as wool pulp fibers or cotton linters, in amounts of about 75 to about 98%, and balance being textile length fibers such as rayon as described in U.S. Pat. No. 3,663,348 to Liloia et al.

Facing sheet materials suitable for use in this invention have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$, is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 12 may also be made of an apertured, non-woven fabric which is formed, for example, in accordance with the teachings in commonly assigned U.S. Pat. Nos. 2,862,251; 3,081,514; and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers or blends thereof. Typical facing layers made of a polyester-type material can have a weight of ¾ oz./yd.$^2$.

In addition, facing sheet 12 can be formed of a non-apertured material, such as a nonwoven isotropic web, sponge, or the like. In all of the aforementioned facings, the materials should be relatively hydrophobic so as to retard wicking within the facing layer.

Highly moisture-absorbent fibrous pad or batt 15 which is substantially rectangular in shape, but usually smaller than the facing and backing sheet, is centrally disposed therebetween. Pad 15 can be formed in accordance with the teachings of U.S. Pat. No. 3,612,055 to Mesek et al. Alternatively, a higher moisture-absorbent layer can be provided substantially coextensive with backing sheet 11, if desired.

Typical disposable diapers which can be fitted with a tab-type fastener described hereinabove are shown in U.S. Pat. No. 3,612,055 to Mesek et al. and in U.S. Pat. No. 3,683,916 to Mesek et al. Other suitable disposable diaper structures are shown in U.S. Pat. No. Re. 26,151 to Duncan et al.

Release properties can be imparted to release regions 16 and 17 by coating the surfaces thereof with a silicone compound, or the like. Appropriate release formulations suitable for this purpose are well known in the art.

The pressure-sensitive adhesive layer for providing a tacky surface on tab fastener working ends is formed by applying a pressure-sensitive adhesive known in the art to the appropriate tab surface. The applied adhesive shall have good tack, good cohesive strength, good resistance to moisture and good resistance go aging. Illustrative of such adhesives are mixtures of natural or synthetic rubber, zinc oxide, and various resins, also latices of natural or synthetic rubber, or water dispersions of acrylic tacky polymers or copolymers.

In use, a diaper equipped with tab fasteners of this invention is applied to the infant by laying out the diaper on a suitable relatively flat surface and positioning the infant thereon so that the waist-underlying end of the diaper is that having tab fasteners 18 and 19. The other end of the diaper then extends downwardly between the infant's legs. Next, the downwardly-extending end of the diaper is brought up between the infant's legs to a position contiguous with the front of the infant's waist. The diaper is thereafter secured to the infant by placing the corners of the waist portion of the abdomen covering end as far around the infant's waist as they will go and by bringing the corners of the waist-underlying end of the diaper into an overlapping relationship with the aforementioned corners so that the diaper snugly encircles the infant's waist. The removably attached terminal portions of the tab fasteners, i.e., free working ends 22 and 23, are then lifted from corresponding release surfaces 16 and 17 by using pull strings 24 and 25. Thereafter free working ends 22 and 23 are adhesively fixed in a desired position on diaper backing sheet 11 of the abdomencovering end of the diaper by urging the pressure-sensitive adhesive surfaces of free working ends 22 and 23 in contact with the respective underlying backing sheet regions.

The foregoing description and the drawing are illustrative but are not to be taken as limiting. Still other variations and modifications are possible without departing from the spirit and scope of this invention.

I claim:

1. A disposable diaper which comprises a moisture-impermeable backing sheet forming a diaper outside surface for direction away from an infant when the diaper is worn by that infant, a moisture-retaining layer adhered to the backing sheet and having a fibrous facing which forms a diaper inside surface for direction toward the infant, a release region directly on said fibrous facing and situated on and extending inwardly from longitudinal margin of the diaper, tab fastener means having a fixed end secured to said diaper backing sheet and a free working end removably attached to said release region, and pull string means attached to said free working end for separating said free working end from the underlying release region.

2. The disposable diaper in accordance with claim 1 wherein said release region is of an area greater than said free working end.

3. The disposable diaper in accordance with claim 1 wherein said pull string means is a string segment adhesively attached to said free working end.

4. The disposable diaper in accordance with claim 1 wherein said release region is a flexible strip of sheet material coated with a release composition and permanently attached to said facing sheet on the diaper inside surface.

5. The disposable diaper in accordance with claim 1 wherein said release region is a portion of facing surface bearing a release composition.

6. The disposable diaper in accordance with claim 1 wherein a release region is provided on and extending inwardly from each opposed longitudinal margin of the diaper and wherein both of said release regions are terminal portions of a release-coated strip laced through said facing sheet transversely across the diaper.

* * * * *